US009651513B2

(12) United States Patent
Dunlap et al.

(10) Patent No.: US 9,651,513 B2
(45) Date of Patent: May 16, 2017

(54) FINGERPRINT SENSOR AND BUTTON COMBINATIONS AND METHODS OF MAKING SAME

(71) Applicant: Synaptics Incorporated, San Jose, CA (US)

(72) Inventors: Brett Dunlap, Queen Creek, AZ (US); Paul Wickboldt, Walnut Creek, CA (US)

(73) Assignee: Synaptics Incorporated, San Jose, CA (US)

( * ) Notice: Subject to any disclaimer, the term of this patent is extended or adjusted under 35 U.S.C. 154(b) by 643 days.

(21) Appl. No.: 14/050,012

(22) Filed: Oct. 9, 2013

(65) Prior Publication Data

US 2014/0103943 A1    Apr. 17, 2014

Related U.S. Application Data

(60) Provisional application No. 61/713,550, filed on Oct. 14, 2012, provisional application No. 61/754,287, filed on Jan. 18, 2013.

(51) Int. Cl.
*G01R 27/26* (2006.01)
*G01N 27/22* (2006.01)
*G06K 9/00* (2006.01)

(52) U.S. Cl.
CPC ....... *G01N 27/221* (2013.01); *G06K 9/00053* (2013.01)

(58) Field of Classification Search
CPC . G06K 9/0002; G06K 9/00053; G01N 27/221
See application file for complete search history.

(56) References Cited

U.S. PATENT DOCUMENTS 5,748,441 A   5/1998 Loritz et al.
6,188,391 B1  2/2001 Seely et al.
(Continued)

FOREIGN PATENT DOCUMENTS

CN   101034432 A   9/2007
CN     1983336 B   8/2010
(Continued)

OTHER PUBLICATIONS

Taiwan Patent Office Search Report; Taiwan Application No. 102111264; Apr. 29, 2016.
(Continued)

*Primary Examiner* — Daniel Miller
(74) *Attorney, Agent, or Firm* — Leydig, Voit & Mayer, LTD

(57) ABSTRACT

It will be understood by those skilled in the art that there is disclosed in the present application a biometric sensor that may comprise a plurality of a first type of signal traces formed on a first surface of a first layer of a multi-layer laminate package; at least one trace of a second type, formed on a second surface of the first layer or on a first surface of a second layer of the multi-layer laminate package; and connection vias in at least the first layer electrically connecting the signal traces of the first type or the signal traces of the second type to respective circuitry of the respective first or second type contained in an integrated circuit physically and electrically connected to one of the first layer, the second layer or a third layer of the multi-layer laminate package.

19 Claims, 14 Drawing Sheets

(56) References Cited

U.S. PATENT DOCUMENTS

| | | |
|---|---|---|
| 6,337,919 B1 | 1/2002 | Duton |
| 6,522,773 B1 | 2/2003 | Houdeau |
| 6,710,461 B2 | 3/2004 | Chou et al. |
| 6,795,569 B1 | 9/2004 | Setlak |
| 6,912,299 B1 | 6/2005 | Hoshino |
| 7,030,860 B1 | 4/2006 | Hsu et al. |
| 7,251,351 B2 | 7/2007 | Mathiassen et al. |
| 7,848,550 B2 | 12/2010 | Mathiassen et al. |
| 8,018,065 B2 | 9/2011 | Lam |
| 2004/0123113 A1 | 6/2004 | Mathiassen et al. |
| 2006/0140461 A1 | 6/2006 | Kim et al. |
| 2008/0054875 A1 | 3/2008 | Saito |
| 2008/0238878 A1 | 10/2008 | Wang |
| 2010/0321159 A1 | 12/2010 | Stewart |
| 2011/0090047 A1 | 4/2011 | Patel |
| 2011/0215484 A1* | 9/2011 | Bond ................... G06K 9/0002 257/787 |
| 2011/0298711 A1 | 12/2011 | Dean et al. |
| 2011/0304001 A1 | 12/2011 | Erhart et al. |
| 2012/0134549 A1 | 5/2012 | Benkley, III |
| 2012/0256280 A1 | 10/2012 | Erhart |
| 2013/0259329 A1 | 10/2013 | Wickboldt et al. |
| 2013/0279769 A1* | 10/2013 | Benkley, III ....... G06K 9/00013 382/124 |

FOREIGN PATENT DOCUMENTS

| | | |
|---|---|---|
| CN | 101933051 A | 12/2010 |
| JP | 2002/330202 | 11/2002 |
| TW | 200919255 A | 5/2009 |
| TW | 201113992 A | 4/2011 |

OTHER PUBLICATIONS

Taiwan Patent Office Search Report; Taiwan Application No. 102136931; Nov. 23, 2016.

* cited by examiner

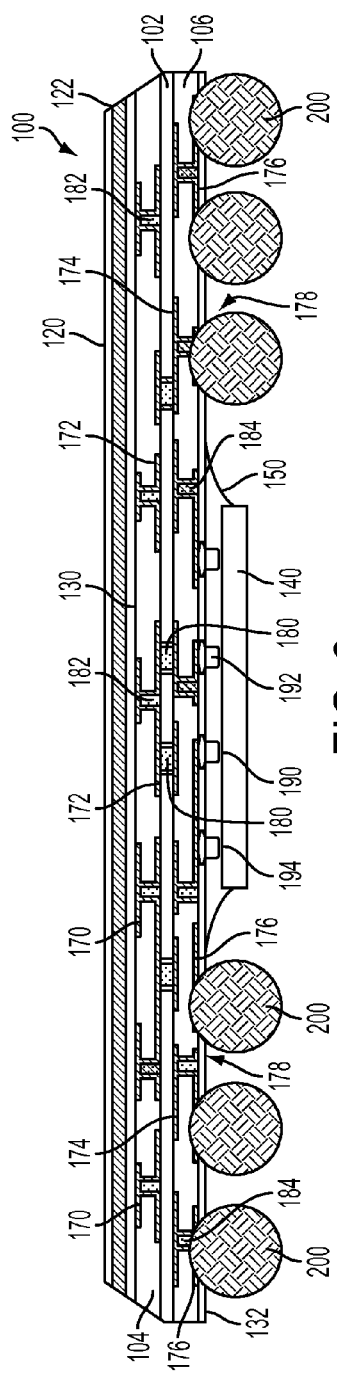
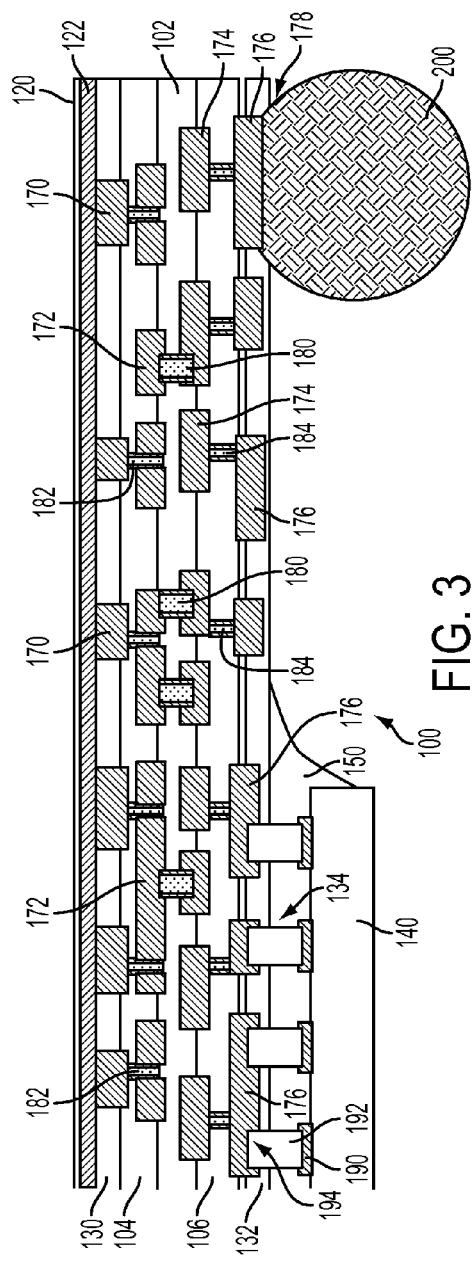
FIG. 2
FIG. 3

FINGERPRINT SENSOR AND BUTTON COMBINATIONS AND METHODS OF MAKING SAME

CROSS-REFERENCE

This application claims priority to U.S. Provisional Patent Application Ser. Nos. 61/713,550, filed on Oct. 14, 2012, entitled FINGERPRINT SENSOR HAVING FLIP CHIP PACKAGING and 61/754,287, filed on Jan. 18, 2013, entitled COMPACT BUTTON CONFIGURATIONS AND METHODS, the contents of which are incorporated herein.

BACKGROUND OF THE INVENTION

Biometric sensors and imagers, including, e.g., fingerprint sensors and imagers like those disclosed in the present application are known in the art and are disclosed, e.g., in U.S. Pat. No. 7,099,496 to Benkley, issued Aug. 29, 2006, for SWIPED APERTURE CAPACITIVE FINGERPRINT SENSING SYSTEMS AND METHODS; U.S. Pat. No. 7,463,756 to Benkley, issued Dec. 9, 2009, for FINGER POSITION SENSING METHODS AND APPARATUS; U.S. Pat. No. 8,165,355 to Benkley, issued Apr. 24, 2012, for METHOD AND APPARATUS FOR FINGERPRINT MOTION TRACKING USING AN IN-LINE ARRAY FOR USE IN NAVIGATION APPLICATIONS; U.S. Pat. No. 7,751,601 to Benkley, issued Jul. 6, 2010, for FINGER SENSING ASSEMBLIES AND METHODS OF MAKING; and US Patent Application Publication Nos. US2011/0304001, published Dec. 15, 2011, entitled FINGERPRINT SENSING CIRCUIT; US2012/0189166 published Jul. 26, 2012, entitled USER INPUT UTILIZING DUAL LINE SCANNER APPARATUS AND METHOD; and US2012/0256280, published Oct. 11, 2012, entitled PACKAGING FOR FINGERPRINT SENSOR AND METHOD OF MANUFACTURE. As these types of sensors are used in more and more forms of portable/mobile computing/communications devices, such as cell phones, Blackberries, and other forms of personal digital assistants ("PDAS"), electronic pads, tablets, notebooks, etc. (collectively "portable computing devices"), there is a need for both a more miniaturized, especially thinner, and durable sensor device.

Such sensors have also been incorporated into and/or integrated with such user portable/mobile computing/communications devices and, in particular can be integrated with a button on such a user device that performs some other function for the user device other than gathering biometric data for user authentication or other uses. It has become important, therefore, for such sensors, when so incorporated/integrated, to be durable and able to survive somewhat extreme conditions of stress, as an example, during failure testing, such as drop testing, and then later while in actual use. The present application addresses various aspects of this need in the art.

Since its inception, fingerprint sensing technology has revolutionized biometric identification and authentication processes. In most cases, a single fingerprint can be used to uniquely identify an individual in a manner that cannot be easily replicated or imitated. The ability to capture and store fingerprint image data in a digital file of minimal size has yielded immense benefits in fields such as law enforcement, forensics, and information security.

However, the widespread adoption of fingerprint sensing technology in a broad range of applications has faced a number of obstacles. Among these obstacles is the need for a separate and distinct apparatus for capturing a fingerprint image. Additionally, such components are often impractical for use in systems that are designed to be of minimal size or weight. As handheld devices begin to take on a greater range of functionality and more widespread use, engineers and designers of such devices are constantly seeking ways to maximize sophistication and ease of use while minimizing size and cost. Typically, such devices only incorporate input/output components that are deemed to be essential to core functionality, e.g., a screen, and a limited set of buttons.

For these reasons, fingerprint-based authentication techniques have not replaced username and password authentication in the most common information security applications such as email, online banking, and social networking. Paradoxically, the growing amount of sensitive information Internet users are entrusting to remote computer systems has intensified the need for authentication procedures more reliable than password-based techniques.

An electronic device having a button interface with built-in fingerprint sensing capability would thus lead to increased adoption of fingerprint-based authentication. As will be seen, the present disclosure provides such a system that overcomes obstacles associated with incorporating a fingerprint sensor into an electronic device button interface.

SUMMARY

It will be understood by those skilled in the art that there is disclosed in the present application a biometric sensor that may comprise a plurality of a first type of signal traces formed on a first surface of a first layer of a multi-layer laminate package; at least one trace of a second type, formed on a second surface of the first layer or on a first surface of a second layer of the multi-layer laminate package; and connection vias in at least the first layer electrically connecting the signal traces of the first type or the signal traces of the second type to respective circuitry of the respective first or second type contained in an integrated circuit physically and electrically connected to one of the first layer, the second layer or a third layer of the multi-layer laminate package. The first type of signal trace may comprise drive signal traces and the second type of traces may comprise at least one receive signal trace or the first type of traces may receive signal traces and the second type of traces comprising at least one drive signal trace. The at least one trace of the second type may comprise one trace of the second type and the sensor may comprise a one dimensional linear array capacitive gap biometric sensor. The at least one trace of the second type may comprise a plurality of traces of the second type and the sensor may comprise a two dimensional grid array capacitive gap biometric sensor.

The first layer may comprise a circuit board layer and the second layer may comprise a core layer attached to one side of the circuit board layer. A third layer comprising a circuit board layer may be attached to another side of the core layer. The biometric sensor may be encapsulated on all sides except for a top finger sensing side and may be attached to a substrate. The biometric sensor may be encapsulated on all sides. The biometric sensor may be encapsulated by moldable plastic material formed around the package by a molding process, which also may form an encapsulation molded with rounded edges and corners. The biometric sensor may comprise a biometric sensor mounted on a portable electronic device, and may also cooperate mechanically with elements of a switch, e.g., within the housing of the portable computing device, to operate the switch, i.e., act as a switch operating button.

A user interface, e.g., a button, suitable for incorporation into an electronic device, such as a laptop, tablet, or smart phone or other portable computing devices is disclosed, as well as methods of use and methods of manufacture. The interface can have a housing with a small profile with a thickness less than or equal to 3 mm, an upper layer which fits within a user device housing and sits atop one or more sets of sensor traces in communication with a chip external to the interface via a flexible circuit.

An aspect of the disclosure is directed to an electronic device user interface. Suitable electronic device user interfaces can comprise: a housing having side walls defining an open upper end and a lower surface; a biometric sensor capable of sensing a target biometric parameter having a sensor interface with a sensing side wherein the sensor interface is capable of positioning within the open upper end of the housing; a protective coating on the sensing side of the sensor interface; and an integrated circuit, external to the housing, in communication with the biometric sensor. In some aspects, the protective coating extends over or through one or more side walls of the housing.

Additionally, the biometric sensor further can comprise a flexible circuit substrate and at least one conductive trace connecting the biometric sensor to the integrated circuit. The conductive traces of the flexible circuit substrate can also be positionable on at least one of a side of the flexible circuit substrate facing towards an exterior of the housing and a side of the flexible circuit substrate facing towards an interior of the housing. In some configurations, the device can further comprise one or more of each of: a potting material positionable between the lower surface of the housing and the protective coating; a bezel extending from the side walls of the housing above the bottom of the protective covering; and a removable bottom plate that can attach to the housing to support the biometric sensor. In some configurations, the flexible circuit can wrap around the removable bottom plate. Additionally, an adhesive potting material can be provided between the bottom plate and the protective coating. In still other aspects, the biometric sensor can be capable of capturing a fingerprint from a finger of a user.

Additional aspects of the disclosure are directed to a method of fabricating an electronic device user interface. The method can comprise: providing a biometric sensor having a sensor interface with a sensing side and one or more conductive traces thereon in communication with a flexible circuit; placing a protective coating on the sensing side of the biometric sensor; inserting the biometric sensor into a housing; and providing an integrated circuit external to the housing in communication with the biometric sensor. An additional step can include: forming the protective coating over one or more side walls of the housing. The biometric sensor can be comprised of a flexible circuit having a flexible substrate, wherein the method further comprises the step of: forming at least one conductive trace connecting the biometric sensor to the integrated circuit.

Yet another step can include forming the one or more conductive traces of the flexible circuit on at least one of a side of the flexible substrate adjacent a finger of a user and a side of the flexible substrate facing away from the finger. Still other steps can include one or more of each of: providing an adhesive between the bottom portion of the housing and the protective coating; forming a bezel over at least the edges of the protective covering; providing a bottom plate that attaches to the housing to enclose the biometric sensor; forming the flexible circuit around the bottom plate; and providing an adhesive between the bottom plate and the protective coating.

Still another aspect of the disclosure is directed to a method of using an electronic device user interface. The method can comprise: providing a housing having side walls defining an open upper end and a lower surface, a biometric sensor capable of sensing a target biometric parameter having a sensor interface with a sensing side wherein the sensor interface is capable of positioning within the open upper end of the housing, a protective coating on the sensing side of the sensor interface, and an integrated circuit, external to the housing, in communication with the biometric sensor; and capturing a fingerprint from a finger of a user when the finger is applied to the biometric sensor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosed subject matter are set forth with particularity in the appended claims. A better understanding of the features and advantages of the present invention will be obtained by reference to the following detailed description that sets forth illustrative embodiments, in which principles of the disclosed subject matter are utilized, and from which they can be illustrated and used, wherein in the accompanying drawings of which:

FIG. 2 shows partly schematically a cross-sectional view generally along the line 2-2 in FIG. 1;

FIG. 3 shows a more detailed version of a portion of the cross-sectional view of FIG. 2;

DETAILED DESCRIPTION

Figure 1:
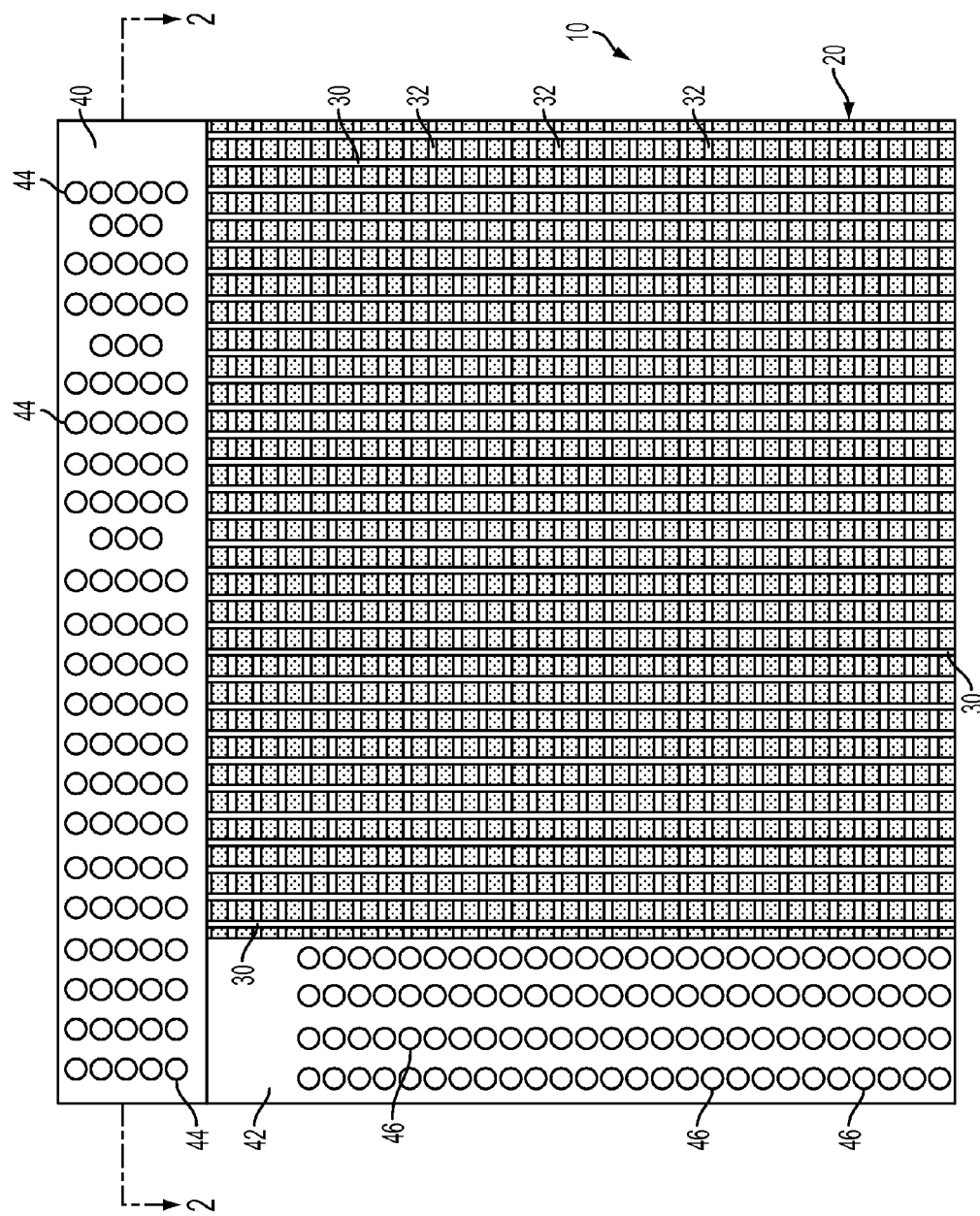
FIG. 1 shows partly schematically an internal portion of a two dimensional ("2D") fingerprint sensor array package/ housing according to aspects of embodiments of the disclosed subject matter.

According to aspects of embodiments of the disclosed subject matter a sensor support housing/package 10, as illustrated schematically in FIG. 1, is disclosed. The sensor 10 may be a biometric sensor, e.g., a fingerprint sensor having a plurality of pixel locations formed in either a linear one dimensional ("1D") array or a two dimensional grid ("2D") array, such as is shown schematically in FIG. 1. As shown by way of example in FIG. 1, the 2D sensor array 10 may form a grid 20, having transmit/drive signal vertical traces 30 and generally perpendicular horizontal receiver signal traces 32. The sensor 10 can also be seen to include a transmit/drive signal via section 40 to the top of the schematic illustration in FIG. 1, including transmit/drive signal vias 44 and a receiver signal via section 42 to the left side of the illustration in FIG. 1, including receiver/response signal vias 46. It will be understood by those skilled in the art that the schematic view of FIG. 1 is not to scale and also does not show all of the vertical traces 30 or horizontal traces 32. It will be understood that usually each of the vias 44 is electrically connected to a vertical trace 30 and each of the vias 46 is connected to a horizontal trace 32, so that there are in reality many more traces 30, 32 than illustrated in FIG. 1.

Assuming that the horizontal traces 32 are in the direction of the width of the finger being sensed, the grid 20 would normally be about 12 mm in that direction and would have around 200 traces 32. Ordinarily, for a placement type 2D sensor array 10, the perpendicular vertical traces 30, aligned in the direction of the length of the finger, would be of the same pitch, but would be more in number, e.g., 600, though schematically in FIG. 1 the grid 20 is shown to be square. It will also be understood that the grid 20 could be of 200 horizontal traces 32 across the width of the finger and the vertical traces could be less than 200, e.g., a sufficient number to make the grid 20 a 12 mm×4 mm grid array, by way of example, such as for a swipe sensor where the sensor captures so called frames of, e.g., from 66 horizontal traces, forming scanned frames that can be reconstructed to form the entire fingerprint image, as is well understood in the art. It will also be understood that the disclosed subject matter could support the packaging of a linear one dimensional capacitive gap array, where there are many vertical traces 30 but only one horizontal trace 32, usually but not exclusively co-planer with the vertical traces 30, and acting as a transmitter plate to the many perpendicular receiver plates 30 or a receiver plate to the many perpendicular transmitter plates 30 facing the single plate across a gap, e.g., forming a one dimensional linear capacitive gap array. It will also be understood that, as elsewhere discussed in the present application there is generally at least one layer between the horizontal traces 32 and the vertical traces 30, in a 2D grid array, which layer(s) is not shown in FIG. 1.

Turning now to FIGS. 2 and 3, there is shown partly schematically a first cross-sectional view and an enlargement of that view, generally along the line 2-2 in FIG. 1. FIG. 2 shows in cross-section view a sensor support housing/package 100, having a core layer 102, having a thickness of about 100μ, ±20μ, an upper micro-printed circuit board ("PCB") laminate layer 104, having a thickness of about 75μ, ±10μ, and a lower micro-PCB laminate layer 106, having a thickness of about 75μ, ±10μ on either side of the core layer 102. A transparent protective glass layer 120, having a thickness of about 10μ, ±5μ, and an opaque ink rigid protective layer 122, having a thickness of about 15μ, ±5μ, along with an upper solder mask layer 130, having a thickness of about 25μ, ±8μ, are arranged above the upper micro-PCB laminate layer 104. A lower solder mask layer 132, having a thickness of about 25μ, ±8μ, lies below the lower micro-PCB laminate layer 106. These layers form a composite laminate forming a pin grid array ("PGA") package 100, to which an integrated circuit die 140, having a thickness of about 150μ, ±12μ, may be attached using an under fill layer 150, having a thickness of about 70μ, ±10μ.

Upper micro-PCB laminate top traces 170, may be formed partly in the upper micro-PCB laminate layer 104 and partly in the upper solder mask layer 130. Upper micro-PCB laminate layer bottom traces 172, may be formed, partly in the upper micro-PCB laminate layer 104 and partly in the core layer 102. Lower micro-PCB laminate layer top traces 174, may be formed partly in the lower micro-PCB laminate layer 106 and partly in the core layer 102. Lower micro-PCB laminate bottom traces 176, may be formed partly in the lower micro-PCB laminate layer 106 and partly in the lower solder mask layer 132.

Die connective pads 190 may be formed on the back side of the integrated circuit die 140, and have attached to each of them a die connective stud 192, as can be seen in more detail, e.g., in FIG. 3, which may be formed on the die 140, e.g., through openings in a mask layer on the back side of the die 140, which may later be removed. The studs 192 may then be surrounded in the under fill layer 150 and serve to electrically connect a respective die connective pad 190 to a respective die connective stud 192, which in turn connects through an opening 134 in the lower solder mask layer 132 to a respective lower micro-PCB laminate layer bottom trace 176, e.g., through a bump 194 that may be grown on the respective stud 192 and formed, e.g., of solder.

Core layer 102 vias 180, e.g., connecting a respective upper micro-PCB laminate bottom trace 172 to a respective lower micro-PCB laminate top trace 174 may be formed through the core layer 102, e.g., by laser drilling. Upper micro-PCB laminate layer vias 182, e.g., connecting an upper micro-PCB laminate layer top trace 170 to a respective upper micro-PCB laminate bottom trace 172, may similarly be formed through the upper micro-PCB laminate layer 104. Lower micro-PCB laminate layer vias 184, e.g., connecting a lower micro-PCB laminate top trace 174 to a respective lower micro-PCB laminate layer bottom trace 176, may similarly be formed through the lower micro-PCB layer 106.

The die contact plates 190, grown on the wafer substrate forming the die 140, may be made of any suitable conductive material, such as aluminum ("Al"), copper ("Cu") or gold ("Au"), while the contact studs 192 may also be made from a suitable conductive material, e.g., Cu. The contact bumps 194 may be made, e.g., of solder and grown on the top of the contact posts 192, after they are formed or while the masking material still covers the back side of the die 140 and may extend through openings 178 formed in the lower solder mask layer 132.

Figure 5:
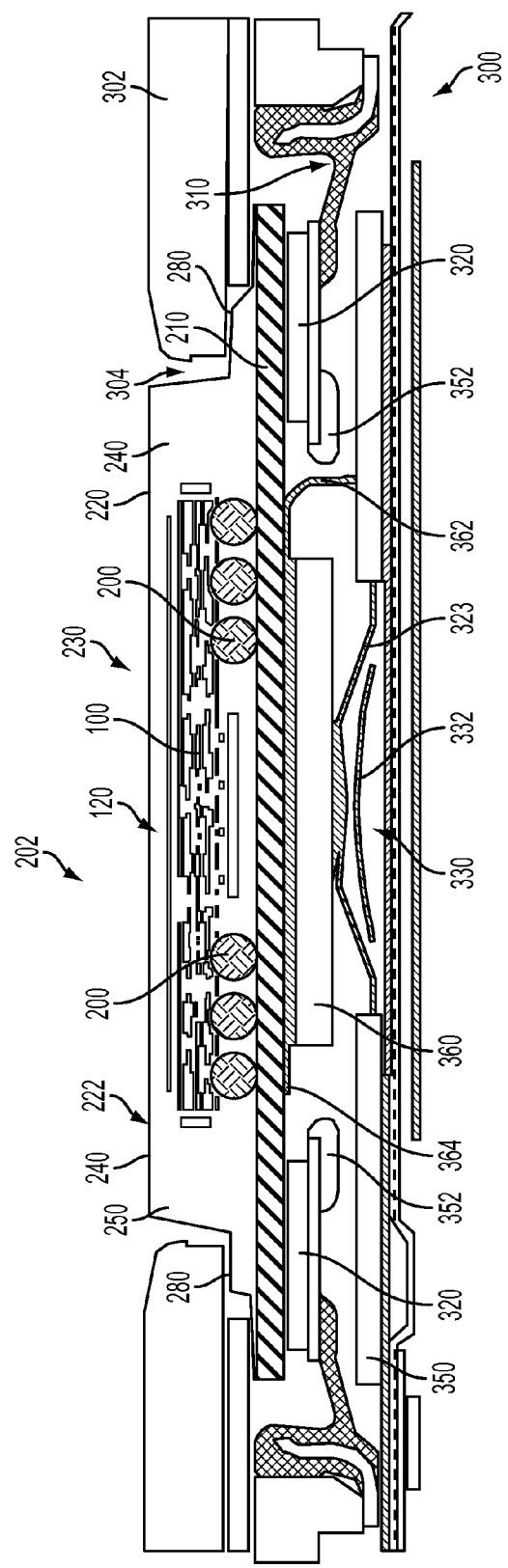
FIG. 5 shows a cross-sectional view of a sensor button switch assembly for a mobile communication device, according to aspects of embodiments of the disclosed subject matter.
Figure 9:
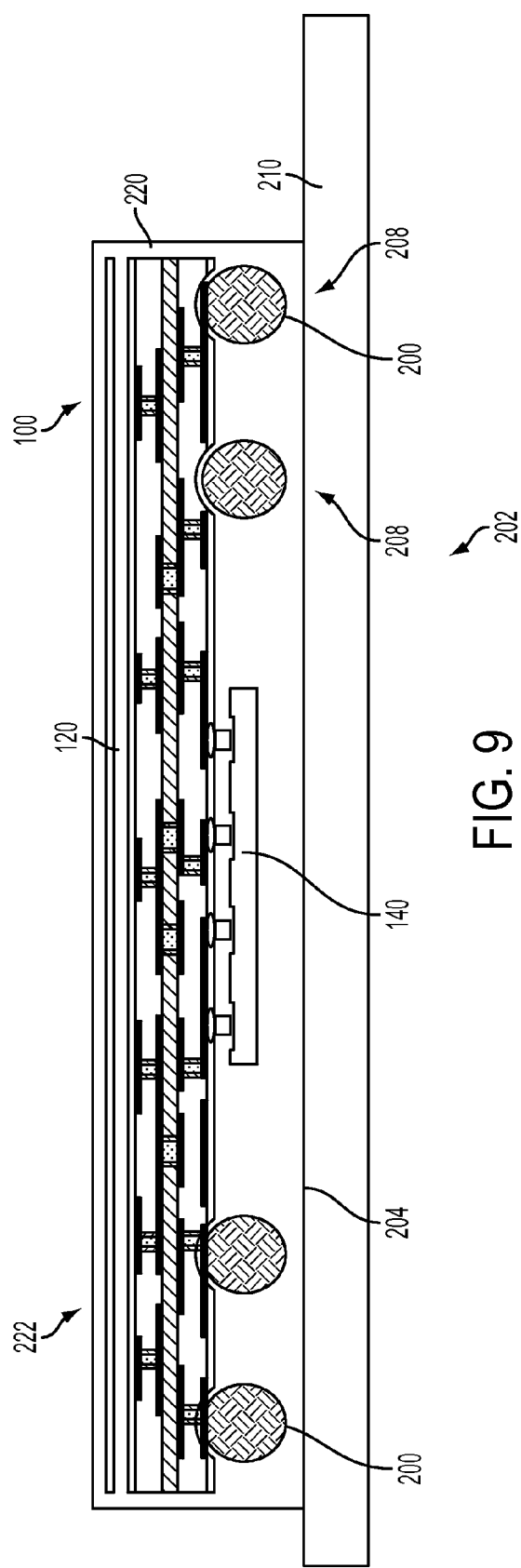
FIG. 9 shows a cross-sectional view of a portion of FIG. 5.

Ball grid array ("BGA") solder balls 200 may extend through openings 178 in the lower solder mask layer 132 and make electrical contact with lower micro-PCB laminate layer bottom traces 176, e.g., to connect the package 100 to other electrical components of the sensor/imager 10, e.g., through traces on a flexible or rigid substrate, e.g., 210, as shown in FIGS. 5 and 9, on which the package/housing 100 is mounted.

Figure 4:
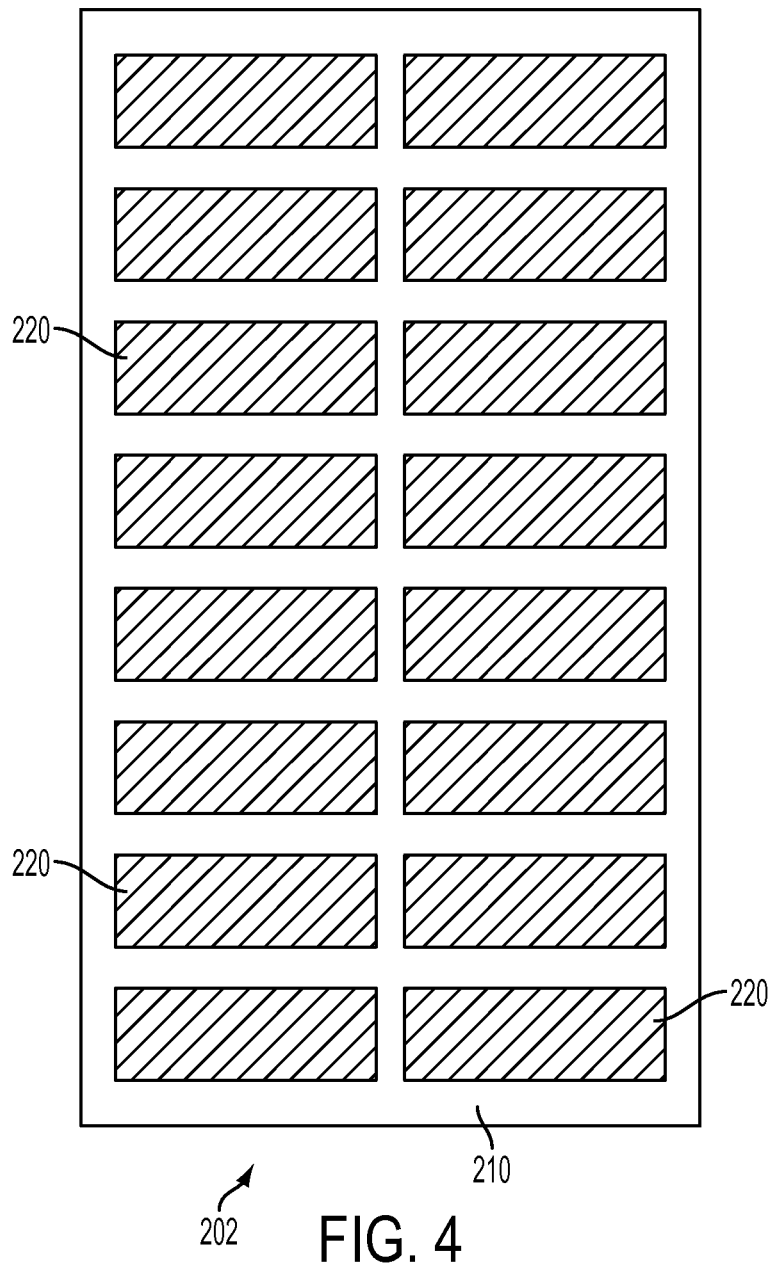
FIG. 4 shows top plan view of a sensor encapsulation assembly according to aspects of embodiments of the disclosed subject matter.

Turning now to FIG. 5 there is shown, by way of example, a sensor encapsulation assembly 202. A flex substrate 210, as illustrated in FIG. 5, can be made from a suitable flexible and dielectric material, such as a polyimide film, like Kapton®. The top plan view of FIG. 4 shows encapsulation material 220 encapsulating the package/housing 100, as is shown in more detail in cross section in FIGS. 5 and 9, with the encapsulation material 220, such as Mold Compound or any number of well known molding compounds, surrounding the package/housing 100, and filling in around the BGA solder balls 200, which may, e.g., make electrical contact to a trace(s) 208 on the flex material 210.

Figure 6:
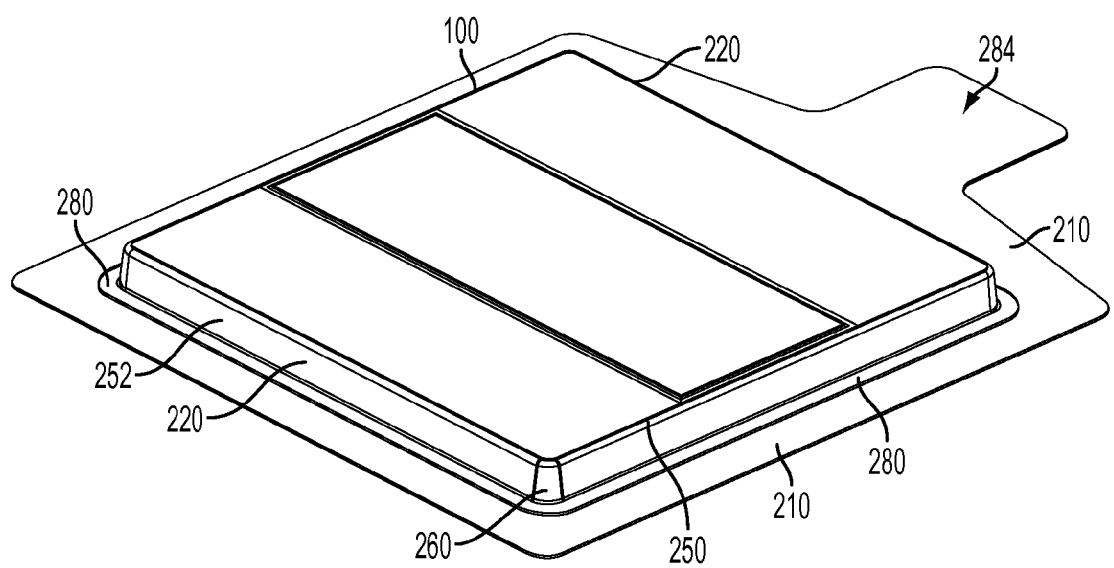
FIG. 6 shows a perspective view of a version of the sensor encapsulation assembly, according to aspects of embodiments of the disclosed subject matter.
Figure 7:
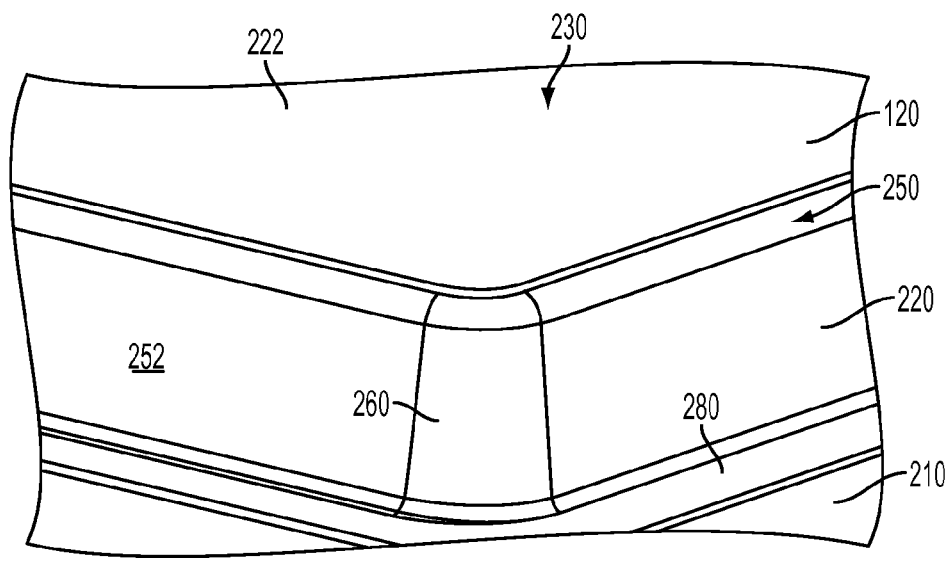
FIG. 7 shows a more detailed view of a portion of FIG. 6.
Figure 8:
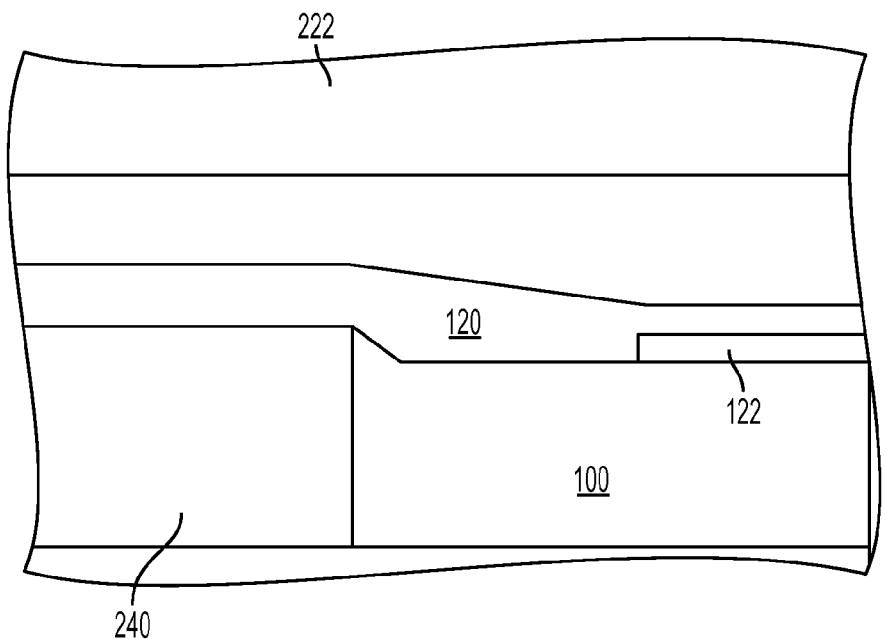
FIG. 8 shows a cross sectional view of an example of a transition from a sensor laminated package to a molded encapsulation, according to aspects of embodiments of the disclosed subject matter.

Turning now to FIG. 5, there in shown in cross section an example of an embodiment of a mobile device biometric sensor and switch combination 300. The mobile device biometric sensor and switch combination 300 fits within an opening 304 in a mobile device housing 302, such that the upper sensor surface 222, formed by the encapsulation material 220 of the housing is generally flush with the outer surface of the mobile device housing 302. The encapsulated sensor package/housing 100 may be mounted on a flexible substrate 210, as shown in FIG. 9 that may be attached to a mobile device waterproof rubber seal member 310, e.g., with a waterproof tape 320. The sensor device package/housing may be entirely encased in the encasing material as illustrated in FIG. 9, or, as shown in FIGS. 5 and 7 the transparent glass layer 120 and overlying hard opaque coating layer 122 may be exposed through an opening 230 in the encapsulating material 220 to facilitate fingerprint sensing. A molded frame/spacer 240, which may be made of the same material as the encapsulating material 220, or, as shown in FIGS. 6-8, may be molded in the encapsulation process. The spacer/frame 240 may have a flange 280, and may serve to hold the encapsulated package/housing 100 on the opening 302. FIG. 8 shows a cross-sectional view of a portion of an exemplary package/housing 100 within, e.g., a sensor encapsulation assembly, surrounded by encapsulation material 220 and covered by a relatively thin layer of rigid material 222, applied as an ink originally and allowed to cure.

The mounting of the package/housing 100 to the flex strip 210 may give the entire assembly enough flexibility such that, when a finger or other object is pressed against the top of the housing, package 100 can move enough to operate an underlying mechanical switch, such as a dome switch 330, which may include a depression member 322 and a deformable contact 332. The switch 330 may be connected to circuitry (not shown) on a circuit board 350 within the body of the mobile device. A toggling two position element 332 may form the other contact of the switch 330, such that when the depression member 322 is moved into the two position element it "clicks" to a non-contacting dome position and the switch 330 is open when the pressure on the package/housing is removed. When the depressing element is moved back into contact with the two position element 332, it is "clicked" back to the contacting position and the switch 330 remains closed when the pressure is removed from the package/housing 100. A pair of stops 352 engaging the circuit board 350 can insure the flex material does not bend to severely, thus damaging the relatively rigid package/housing 100. An interposer plate 360, attached to the bottom of the flexible strip 210, can serve to move the depression member 322, when downward pressure is put on the housing/package 100.

The spacer 240 may be formed with a rounded edge 250, to protect the finger of the user. As shown in more detail, in FIGS. 6-8, instead of a separate spacer 240, the encapsulation material may be initially molded around the package/housing 100 to form, e.g., a slanted side wall 252, rounded corners 260 the rounded top circumference 250 of the molded encapsulation, and the flange 280. In a variation of the process of FIG. 4, the molded encapsulation material 220 may be formed over a package housing 100 attacked to traces on the flexible material substrate 210 formed to have a trace extension 284, which may serve to electrically connect the sensor 10 and IC 140 to other components of the system.

It will be understood by those skilled in the art that according to aspects of embodiments of the disclosed subject matter, the disclosed multi-layer laminate substrate technology has been employed to create a finger print sensor with a very durable package/housing construction, for biometrically authenticating a user of the mobile device and also suitable for use as part of a mobile device mechanical switch, e.g., for turning the mobile device on and off. The sensor may be formed of a 1D or 2D grid array of various shapes and sizes, with one dimension typically at least as wide as normal human finger. The grid can be formed, as an example, by traces forming conducting leads on opposing sides of a top layer in a laminate of layers on opposing sides of a relatively rigid and strong, e.g., reinforced core layer. Electrical drive circuitry may be connected to the traces on one side of the laminate layer and pick-up/response circuitry may be connected to the traces on the opposing side of the upper laminate layer, with the transmit drive traces typically formed closer to the sensing surface of the sensor, i.e., the top surface of the upper laminate layer.

This top surface (top meaning surface closest to the finger during finger print acquisition), as noted, is usually configured as the transmitter traces and the other metal traces on the reverse side of the layer (farther away from the finger), layer is usually configured as the receiver. response signal traces. As is well known in the art, the traces formed in a 1D or 2D array constitute pixel locations where the presence of the finger creates variations in the receive signal response to the transmitted signal, mostly due to variations in the capacitive coupling of the two through the finger near the top of the sensor 10 due to capacitive differences between the presence of a fingerprint valley or ridge in the vicinity of the given pixel location. These variations are detected to generate an finger print image either partly or wholly within the integrated circuit, which can also create the drive signals and time their application to drive signal traces in the grid 10.

It will also be understood that the height of the package/housing can vary based on the BGA size, e.g., in order to conform to differing height requirements. Package/housing size can, e.g., correspond to sensing linear array or grid array area, e.g., about 122 mm across in the direction of the width of the finger and the same or more in the direction of the length of the finger. The package body can, e.g., be square, e.g., in embodiments designed for housing the sensor on the top of or embedded within the housing as required to create a round button. The package may have some or all sides formed with a bevel cut package edge, e.g., down to about a 100μ depth, which may, e.g., be formed in a two pass singulation of individual packages/housings from a plurality of packages/housings formed in one operation as discussed elsewhere in the present application.

A PCB or flex interposer may be required to make a housing in which the package/housing is part of actuating a mechanical switch button. Buttons may be manufactured, e.g., by placing a flex strip(s) in a molding jig. The button housing may, e.g., be molded around the biometric sensor formed within the multilayer flip chip housing/package, e.g., with mold compound surrounding the flip chip placed on the flex strip, e.g., in a row of chips format. The flex strip may form a substrate having, e.g., a thickness of around 80μ-20μ. The top portion of the mold material may have, e.g., a thickness of around 50μ, and a bottom mold thickness of around 1 mm.

According to aspects of embodiments of the disclosed subject matter, a single sided molded package/housing may be created, e.g., having a base substrate, which may be flexible, or rigid, e.g., a PCB or micro-laminated layer PCB, as discussed elsewhere in the present application, by way of illustration, by the mounting of a flip chip laminate package, described in the present application, to the substrate. The assembly, substrate plus flip chip laminate package, can then be place entirely of mostly within an encapsulation material that may then be molded into a desired size and shape, e.g., by the use of moldable encapsulation material, such as well known molding compounds, plastics, resins, etc. The molding material may be used to fill under the flip chip package and/or around the perimeter and/or on the surface of the package to form a molded button. Such a molded button may be utilized solely with the biometric sensor element to sense finger presence and/or surface movement, and, in response, act as a button, or may be combined with an interposer, such as made from a rigid material, like a PCB, or flexible, such as a flex substrate, e.g., to interact with an adjacent mechanical switch when the biometric, i.e., the finger presses down on the sensor area and thus on the entire package/housing.

The substrate/interposer with a flip chip package attached, and encapsulated by use of injection/transfer/compression molding, or the like, may include on the sensing side an encapsulation thickness that is relatively thin, or even non-existent and selected and adjusted to establish a desired sensing distance from the surface of the actual sensing traces in the flip chip package. Sensing distance can be important to accurate data capture. As one option according to aspects of embodiments of the disclosed subject matter, the sensing side of the package can be encapsulated to protect the sensing area from surface, impact, or moisture damage. This can be done, by way of example, in a single molding step, by using materials with filler sizes appropriate for a top minimum thickness. In an example the minimum thickness over the flip chip package can be, e.g., 30-50μ. This thin layer of material would require the use of a fine filler, e.g. one with filler sizes of 15μ, or smaller in the molding compound.

In another example, the assembly can also be encapsulated on all sides with the exception of the upper sensor surface. In such a case, e.g., where the sensor surface is not encapsulated, it can be protected by applying protective coating, e.g., as noted elsewhere, a spray ink coating that hardens as it is cured, and/or a glass or other transparent plastic coating, of, e.g., by a second molding step. The protective coating/coatings to the surface of an exposed flip chip laminate substrate and/or encapsulating area is contemplated.

In a third option another variant may be to add a protective coating/coatings to the surface of the flip chip package prior to assembly on the button substrate and further encapsulation. Such an encapsulation molding process can allow for a wide variety of customization of button sizes and shapes with a single flip chip package/housing by changing of the mold size and shape. Such encapsulation molding processing and materials can also allow radius corners and edges that can not be as easily achieved with standard laminate package technologies.

According to aspects of embodiments of the disclosed subject matter a low cost customizable finger print sensor button, e.g., for the mobile communication device market can be produced. The package/housing body may be, e.g., 10.5 mm×4.0 mm. The package housing may be mounted on a flexible substrate and with supporting components elsewhere on the substrate or on a rigid PCB or a mobile phone board. It is also possible for the flip chip package housing to be mounted to a motherboard with the specified other components also so mounted.

It will be understood by those skilled in the art that there is disclosed in the present application a biometric sensor that may comprise a plurality of a first type of signal traces formed on a first surface of a first layer of a multi-layer laminate package; at least one trace of a second type, formed on a second surface of the first layer or on a first surface of a second layer of the multi-layer laminate package; and connection vias in at least the first layer electrically connecting the signal traces of the first type or the signal traces of the second type to respective circuitry of the respective first or second type contained in an integrated circuit physically and electrically connected to one of the first layer, the second layer or a third layer of the multi-layer laminate package. The first type of signal trace may comprise drive signal traces and the second type of traces may comprise at least one receive signal trace or the first type of traces comprising receive signal traces and the second type of traces comprising at least one drive signal trace. The at least one trace of the second type may comprise one trace of the second type and the sensor may comprise a one dimensional linear array capacitive gap biometric sensor. The at least one trace of the second type may comprise a plurality of traces of the second type and the sensor may comprise a two dimensional array capacitive biometric sensor.

The first layer may comprise a circuit board layer and the second layer may comprise a core layer attached to one side of the circuit board layer. A third layer comprising a circuit board layer may be attached to another side of the core layer. The biometric sensor may be encapsulated on all sides except for a top finger sensing side and may be attached to a substrate. The biometric sensor may be encapsulated on all sides. The biometric sensor may be encapsulated by moldable plastic material formed around the package by a molding process, which also may form an encapsulation molded with rounded edges and corners. The biometric sensor may comprise a biometric sensor mounted on a portable electronic device, and may also cooperate mechanically with elements of a switch within the portable computing device to operate the switch.

Figure 10A:
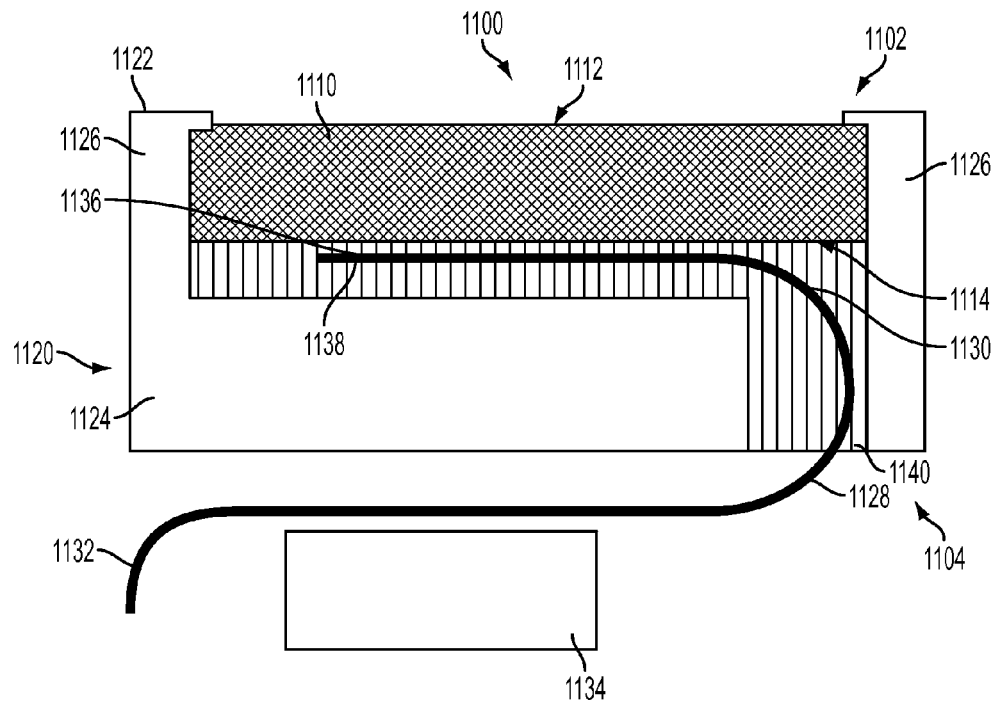
FIGS. 10A-C show a cross-sectional view of an embodiment of a button having a fingerprint sensor incorporated therein.

Turning now to FIG. 10A is a cross-sectional view of an embodiment of a button 1100 having a one dimensional (1D) or two dimensional (2D) biometric sensor 1130, such as a chip on flex (COF) fingerprint sensor 1130, incorporated therein. The button 1100 can have an upper surface 1102 and a lower surface 1104 and may be configurable to provide, for example, a glass or suitable hard coat or film top layer 1110 having an upper surface 1112 and a lower surface 1114, which can be surrounded by a housing 1120 on two or more sides. In this configuration, the edges of the top layer 1110 can be enclosed by a bezel 1122, such as a rim that retains the top layer 1110 within the housing 1120. The upper surface 1112, of the top layer 1110 can serve as an interface for a finger during use of the device and capture of biometric information from the user's finger. The top layer 1110 can be configured to provide protection for the biometric sensor 1130. The top layer 1110 can be composed of different materials and/or colors which may also provide decorative identification. Additionally, the top layer 1110 can be formed from a hard material providing mechanical protection to the sensor tracer elements formed, e.g., on the flexible circuit substrate 1130. The bottom portion of the housing 1120 can also provide mechanical support for the button assembly 1100.

The housing 1120 can be formed from, for example, polycarbonate (PC), acrylonitrile-butadiene-styrene (ABS) or other suitable material, including any thermoplastic characterized by high-impact strength, as well as metals such as aluminum and titanium. The housing 1120 can be configured to have a base 1124, and parallel side walls 1126 (in two dimensional cross-section), an aperture 1128 can be provided through which flexible circuit substrate 1132 of the sensor 1130 passes to connect to the integrated circuit 1134 which can be positioned away from the housing 1120.

The top layer 1110 can be formed from glass or any other suitable material such as shatter resistant substitutes for glass, including polymethylmethacrylate (PMMA), polyethylene terephthalate (PET), etc. The biometric sensor element substrate 1130 can be formed from, for example, from a flexible circuit substrate formed with flex circuit metal tracer elements on top of a flexible film substrate 1132 with the metal traces being in electrical communication with an integrated circuit chip 1134. The integrated circuit chip 1134 need not form part of the stack of materials, and thus, in that configuration, can provide no mechanical functionality to the sensor/finger interface or mechanical operation of the button 1100. An adhesive or potting material 1140 in the aperture, such as thermo-setting plastic or silicone rubber gel, can be provided that secures and/or stabilizes the positioning of the sensor flexible circuit substrate 1130, forming the sensor 1130 in a position between a bottom portion 1124 of the housing 1120 and the top layer 1110 which is engaged by the user during use. The adhesive or potting material 1140 can consist of different regions or layers depending on the assembly method.

Additionally, the adhesive or potting material 1140 may also consist of multiple adhesives or potting materials depending on assembly method and required properties of the button 1100. Dimensions of the form factor could be less than or equal to 900 mm$^2$, less than or equal to 400 mm$^2$, less than or equal to 225 mm$^2$, less than or equal to 100 mm$^2$, in a first two dimensional aspect. In some embodiments the thickness of the form factor is less than or equal to 2 mm or more preferably less than or equal to 1.5 mm. Further embodiments can have the form factor thickness less than or equal to 1 mm.

The potting material 1140 in the opening can be selected such that it provides mechanical support for the sensor 1130. Impact resistance of the button 1100 can be enhanced by maintaining a high hardness (modulus) throughout and/or thin adhesive thickness. Further the silicon integrated circuit (IC) chip 1134 may not be included in this potting area to avoid thermal expansion, humidity expansion and general durability issues that might arise. That is to say, the flexible substrate 1138 can be unfolded from under the button 1100, as illustrated, e.g., in FIG. 14.

As will be appreciated by those skilled in the art, biometric sensors can include, for example, a fingerprint sensor, a velocity sensor, and an integrated circuit which is electrically connected to the fingerprint sensor and the velocity sensor. Biometric sensors can further include sensors adapted and configured to capture one or more parameters of, for example, a fingerprint. Conductive traces (not shown in FIG. 10A) of an image sensor and velocity sensor can be etched or otherwise formed on a side of the flexible circuit substrate 1130 facing the upper surface 1112 of the button 1100. Moreover, the traces can be positioned on the flexible substrate 1130 such that the traces are up (and thus on an upper surface 1136 of the substrate 1132 proximal to the top layer 1110), or the traces are down (and thus on a lower surface 1138 of the substrate distal the top layer 1110). In some configurations, the flex circuit 1130 on the flex substrate 1132 can be configurable to have functionality (i.e., traces formed) on both the upper surface 1336 and the lower surface 1138 which enables the width of the flex 1130 to be reduced, and also reduces the overall package size. Moreover the button 1100 can be part of a mechanically functional switch or a mechanically fixed button. Additionally, the button 1100 can be used for biometric sensing (fingerprint sensing), navigation, or touch sensing.

As will be appreciated in reviewing FIG. 10A, the IC chip 1134 need not be positioned within the stack of materials. Where the IC chip 1134 is positioned away from the stack of materials forming the button, the button 1100 can achieve a more compact profile and lower height which makes the button 1100 more adaptable to be incorporated into an electronic device, such as a smart phone or touch pad. Additionally, the configuration enables the properties (e.g., cover, adhesive material, housing) to be tuned for functionality and durability.

In configurations where the conductive traces are positioned on the top side of the flex 1136, a protective coating can be applied to the upper surface 1136 of the flex substrate 1132 itself, over the image sensor and velocity sensor to provide electrical isolation and mechanical protection of the sensors. Alternatively, conductive traces of an image sensor can be formed on a bottom-side 1138 of a substrate 1132, wherein the substrate 1132 of the flex circuit 1130 acts as a protective coating and can be further improved with a hard coating applied to the upper surface 1136 of the flex circuit 1130 itself.

Further details about fingerprint sensor configurations are contained in, for example, U.S. Pat. No. 7,751,601 to Benkley III for FINGERPRINT SENSING ASSEMBLIES AND METHODS OF MAKING; U.S. Pat. No. 7,099,496 to Benkley III for SWIPED APERTURE CAPACITIVE FINGERPRINT SENSING SYSTEMS AND METHODS; U.S. Pat. No. 7,463,756 to Benkley III for FINGER POSITION SENSING METHODS AND APPARATUS; U.S. Pat. No. 7,460,697 to Erhart et al. for ELECTRONIC FINGERPRINT SENSOR WITH DIFFERENTIAL NOISE CANCELLATION; U.S. Pat. No. 7,146,024 to Benkley III for SWIPED APERTURE CAPACITIVE FINGERPRINT SENSING SYSTEMS AND METHODS; U.S. Pat. No. 6,400,836 to Senior for COMBINED FINGERPRINT ACQUISITION AND CONTROL DEVICE; and U.S. Pat. No. 6,941,001 to Bolle for COMBINED FINGERPRINT ACQUISITION AND CONTROL DEVICE. As will be appreciated by those skilled in the art, the sensor can be a 1D swipe sensor, a 2D touch sensor, a 2D motion sensor, a 2D sensor having two layers of electrodes, a 2D sensor having a single layer of electrodes, a 2D sensor with electrodes on either side of the flex substrate 1130 substrate. Moreover, multiple conductor materials can be used to form the sensor, such that different layers are made from different materials to achieve different results and for different reasons.

The button 1100 can be configurable such that it has a transparent interface, an opaque top coat, or a mask layer, and can be formed such that the upper surface material is not visually transparent. Additionally, the upper surface can be configurable such that it provides a variety of tactile interfaces, e.g., rough or smooth. An "anti-fingerprint and/or anti-smudge" ("AF") and/or a hard coating can be applied.

Figure 10B:
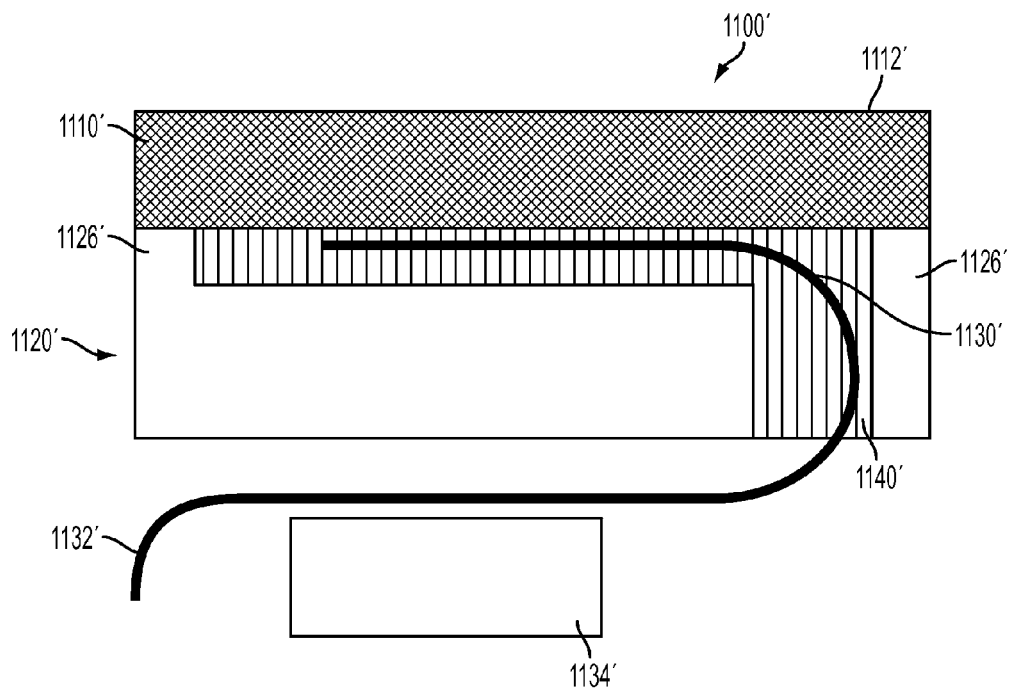

FIG. 10B is a cross-sectional view of another configuration of a button 1100' having a 1D or 2D biometric sensor, such as a COF fingerprint sensor, incorporated therein. In this embodiment the top layer 1110', formed from glass or any other suitable material such as shatter resistant substitutes for glass, including polymethylmethacrylate (PMMA), polyethylene terephthalate (PET), extends at least partly on top of some or all of the sides 1126' of the housing 1120'.

Figure 10C:
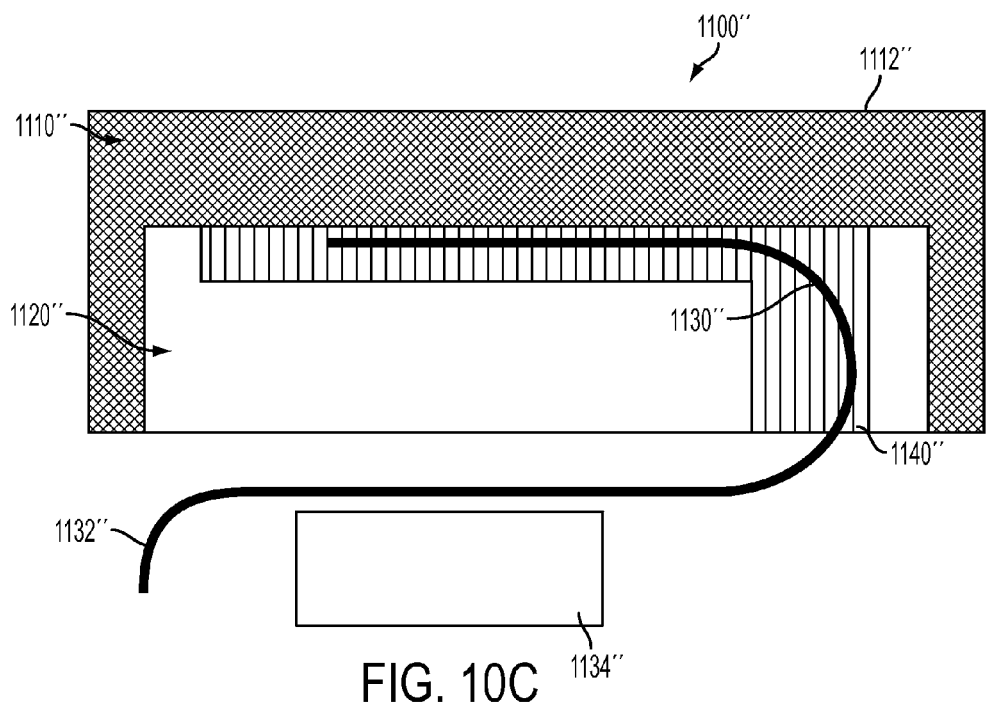

FIG. 10C is a cross-sectional view of another configuration of a button 1100" having a 1D or 2D biometric sensor, such as a COF fingerprint sensor, incorporated therein. In this embodiment the top layer 1110" is over-molded which extends the top layer 1110" over and at least partly surrounds at least one side 1126" of the housing 1120'. This top layer 1110" may be formed by over-molding, wet coating or any suitable method.

Figure 11A:
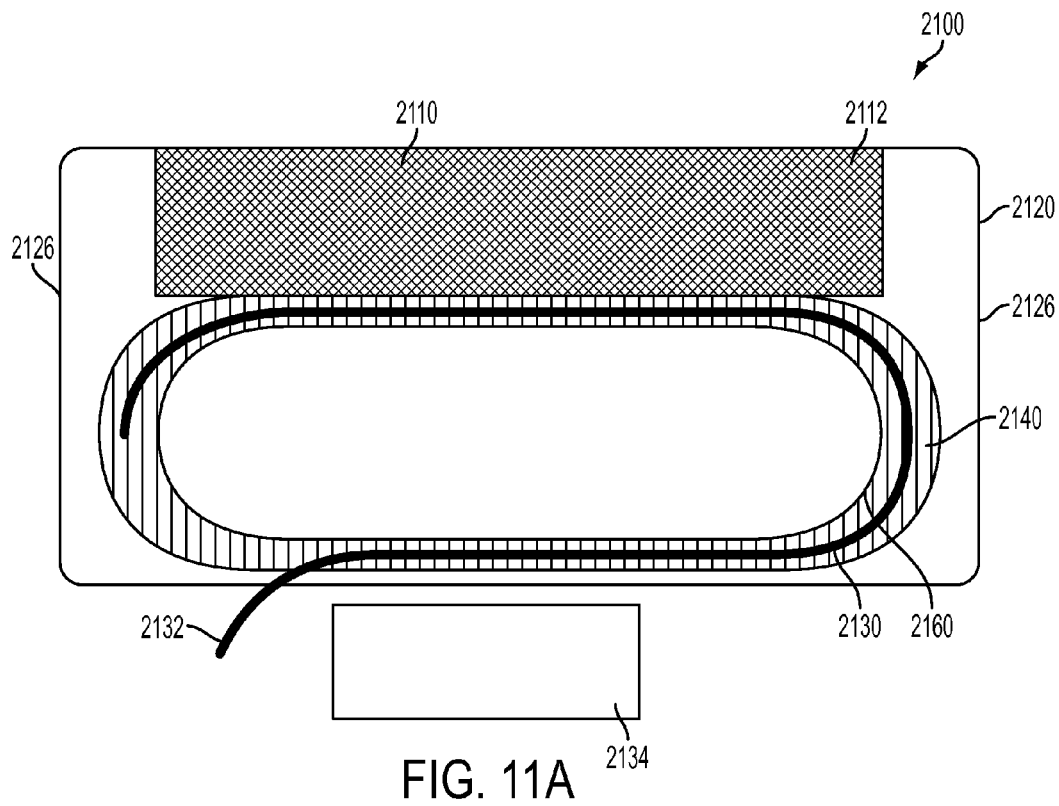
FIGS. 11A-C show a cross-sectional view of another embodiment of a button having a fingerprint sensor incorporated therein.

FIG. 11A is a cross-sectional view of another configuration of a button 2100 having a biometric sensor 2130 incorporated therein. The button 2100 is configurable to provide, for example, a glass or suitable hard coat or film top layer 2110 which is surrounded by a housing 2120. The housing 2120 can be formed from polycarbonate (PC) or other suitable material including but not limited to metals such as aluminum. The biometric sensor 2130 can be comprised, for example, from a flexible circuit substrate 2132 which is in electrical communication with an integrated circuit 2134. This configuration is illustrated to have an adhesive or potting material, 2140 which may or may not be necessary depending on the method of manufacture. The flexible circuit 2132 is secured and/or stabilized about an insert plate or support 2160 that can be fitted within the housing 2120 and, for example, clipped into place. In this configuration the flexible circuit 2132 wraps around the insert or plate 2160 and then the flex/plate combination can be clipped into the housing 2120. In another example the insert or plate can be clipped into the housing 2120 and then the flex substrate 2132 can be wrapped around the plate 2160. Additionally, the plate 2160 may be placed into position within the housing 2120 using an adhesive, e.g., filling the opening 2140, where the flex circuit 2130 fits instead of being clipped into place. Adhesive and/or potting materials may also be optionally used. In some configurations, the glass, hard coat or hard film can be bonded directly to the sensor flexible circuit 2130 flexible substrate 2132 or can be so bonded with an adhesive.

Figure 11B:
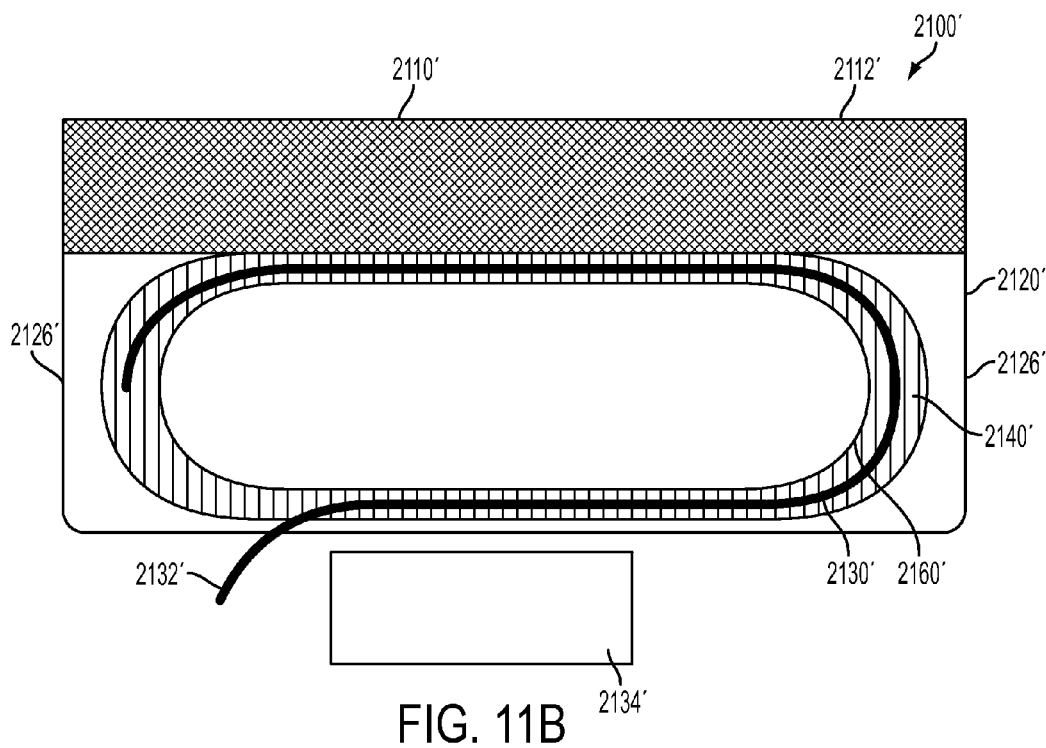

FIG. 11B is a cross-sectional view of another embodiment of a button 2100' having a fingerprint sensor 2130' incorporated therein. The button 2100', containing a flexible substrate 2132' with the sensor elements 2130' wrapped around an insert or plate 2160' in electrical communication with the sensor IC 2134' is configurable to provide, for example, a top layer 2110' that extends at least partly on top of some or all of the sides 2126' of the housing 2120'.

Figure 11C:
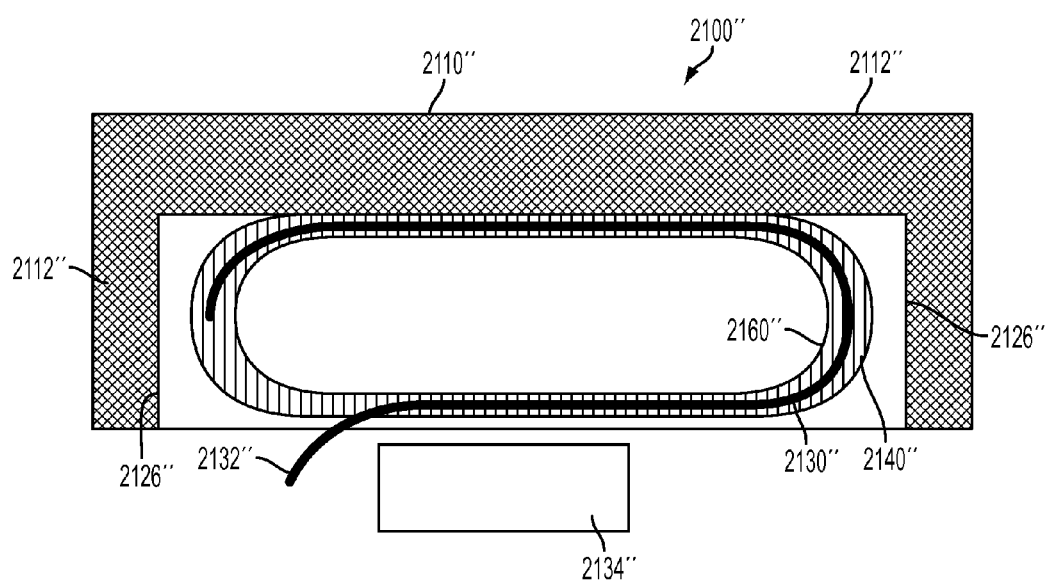

FIG. 11C is a cross-sectional view of another embodiment of a button 2100' having a fingerprint sensor 2130" incorporated therein. The button 2100", containing a flexible substrate 2132" with the sensor elements 2130" wrapped around an insert or plate 2160" in electrical communication with the sensor IC 2134" can be configurable to provide, for example, a top layer 2110" that extends over and at least partly surrounds at least one side of the housing, as shown, e.g., at 2112" on either side of the side walls 2126". This top layer 2110" may be formed by over-molding, wet coating or any suitable method.

Figure 12:
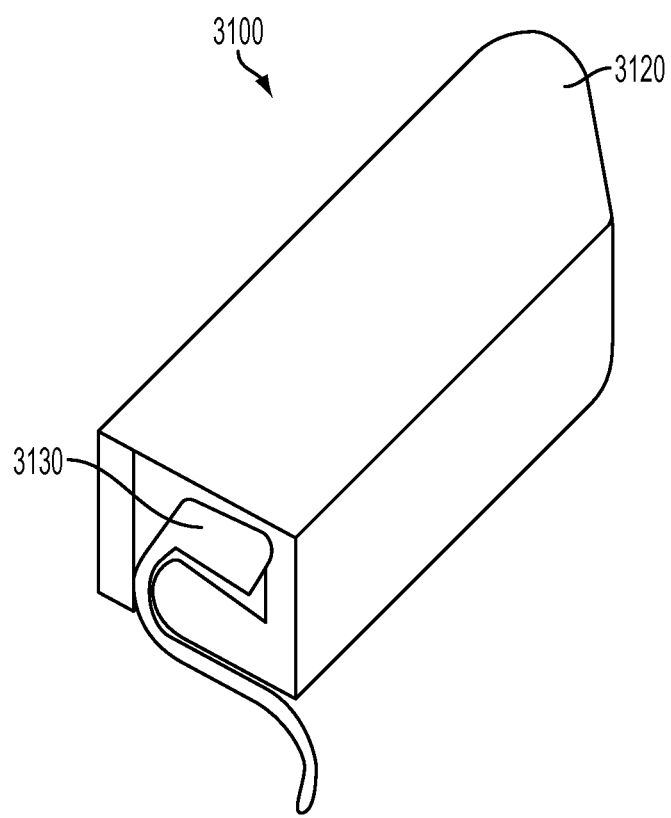
FIG. 12 is a perspective view of a housing with a fingerprint sensor positioned therein.

FIG. 12 is a perspective view of a button 3100 having a housing 3120 with a fingerprint sensor 3130 therein.

Figure 13A:
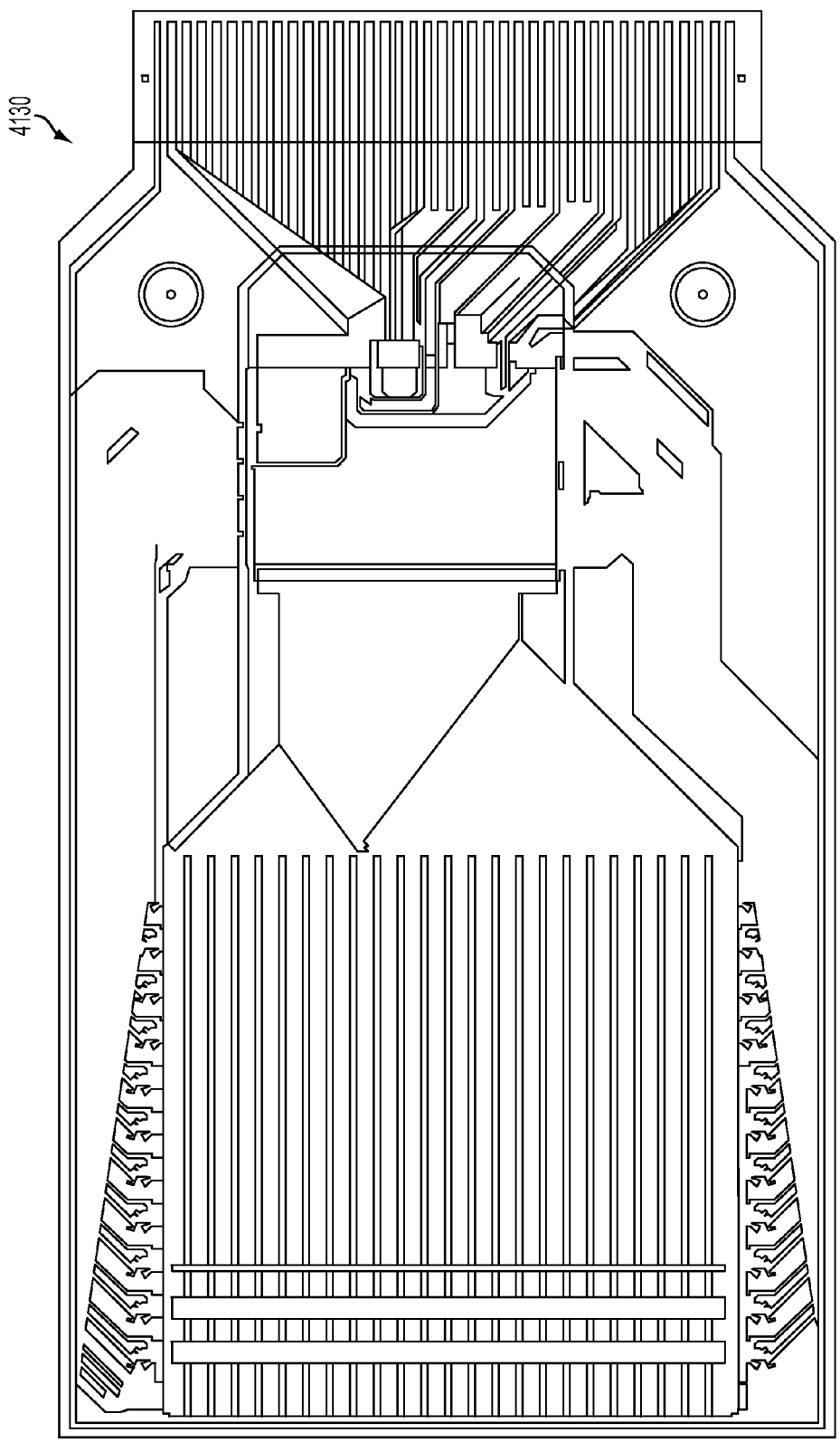
FIGS. 13A-B illustrate fingerprint sensors suitable for use with the button interfaces disclosed herein.
Figure 13B:
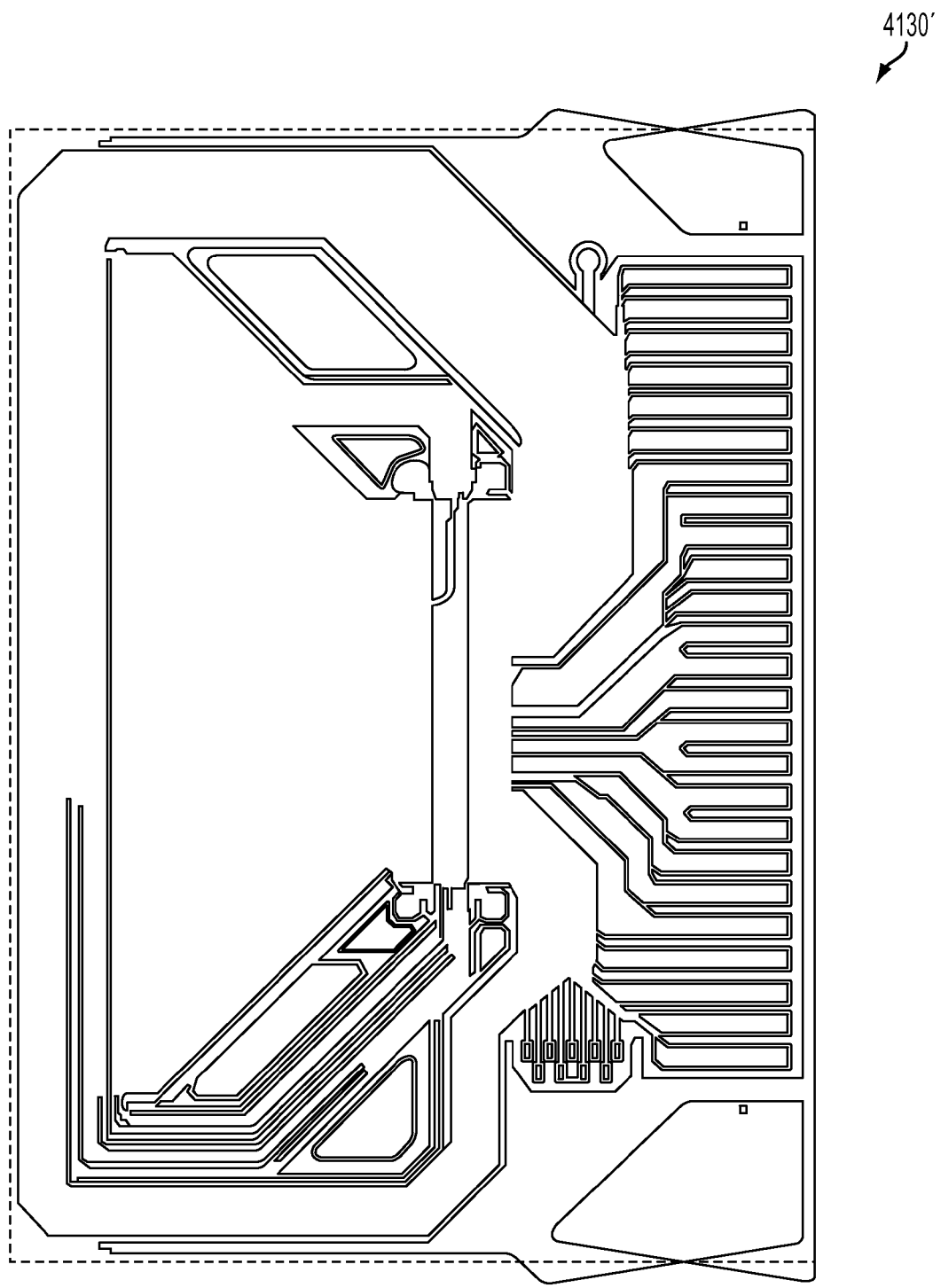

FIGS. 13A-B illustrate fingerprint sensors 130 suitable for use with the button interfaces disclosed herein. Suitable 1D sensors possess from 90 to 300 pixels, or more preferably from 114 to 200 pixels. Suitable 2D sensors possess arrays of pixels in the range of 90 to 300 pixels by 90 to 300 pixels, or more preferentially a range of 114 to 200 pixels by 114 to 200 pixels. A size is from 8 to 30 mm across the broadest length, or more preferably from 6 to 20 mm. FIG. 13A illustrates an example of a 2D touch sensor layout 4130 on flex; FIG. 13B illustrates an example of a 1D sensor layout 4130' on flex.

Figure 14:
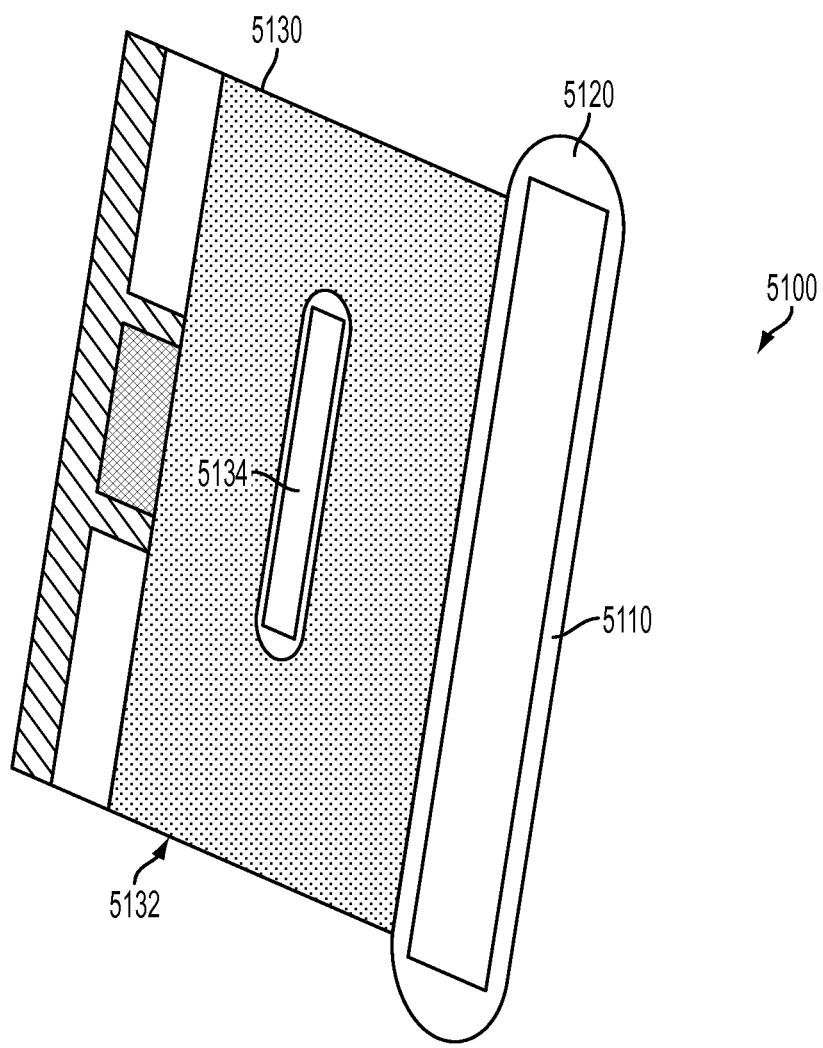
FIG. 14 is an illustration of a button having a fingerprint sensor incorporated therein.

FIG. 14 is an illustration that shows a top view of a button 5100 having a fingerprint sensor incorporated therein. The button 5100 has a pill-shape profile as illustrated, but could be square or circular as required from the implementation. The biometric sensor elements 5130, either 1D or 2D, can be positioned within a portion of the housing 5120 and positioned to be attached to the top layer 5110 (same profile as housing 5120). The flexible substrate 5132 can extend from the embedded sensor such that the substrate 5132 can be wrapped around, for example, a plate (not shown), or otherwise configured to fit within the housing 5120. The integrated circuit 5134 which controls the operation of the sensor/button 5100 is on an opposing end of the flexible substrate 5132 and in electrical communication with the sensor elements in the sensor/button 5100.

II. Methods of Use

The button interfaces may be housed in a host electronic device and configured to perform both object image capture and at least one of an activation of the host device, an activation of a host device function and an input to the host device. The button interfaces may further comprise the button interfaces configured to allow a user to contact the switch simultaneously with providing object image data through an intersection of the at least one drive line and the at least one pickup line. The object may a finger and the button interfaces configured to sense a fingerprint image. The button interfaces described above can also be used to create a functional button (e.g., on/off), to provide navigation functionality, and/or to provide biometric sensing (such as fingerprint sensing).

III. Methods of Manufacture

In one manufacturing example, the button is manufactured according to the following:

Singulate flex by, for example, laser cutting adjoining laminated material.

ACF attach connection to flex may occur prior to singulating flex, after singulating flex or after final button assembly.

Form housing, for example, using a cast or machine.

Provide flex sensor with the ACF board.

Flex bonded to housing.

Assemble housing if needed.

Form top layer either on the flex area only or on the housing only or both the flex and housing. The top layer could be a curable wet coat or cast or hard film bonded with adhesive among other materials.

ACF attach connection to flex if not connected previously.

In another manufacturing example, the button is manufactured according to the following:

Singulate flex.

ACF attach connection to flex may occur prior to singulating flex, after singulating flex or after final button assembly.

Form top layer on the flex area. The top layer could be a curable wet coat or cast or hard film bonded with adhesive among other materials. Applying top layer may occur prior to singulating flex.

Flex bonded to housing.

Housing assembled if needed.

ACF attach connection to flex if not connected previously.

In still another manufacturing example, the button is manufactured according to the following:

Singulate flex.

ACF attach connection to flex may occur prior to singulating flex, after singulating flex or after final button assembly.

Top layer bonded to housing. The top layer could be a curable wet coat or cast or hard film bonded with adhesive among other materials.

Bond flex to top layer and/or housing.

Form support behind flex either by filling using an epoxy and/or bond plate in place.

ACF attach connection to flex if not connected previously.

In a fourth manufacturing example, the button is manufactured according to the following:

Singulate flex.

ACF attach connection to flex may occur prior to singulating flex, after singulating flex or after final button assembly.

Attach flex to the bottom plate of the housing.

Attach plate/flex combination to the housing.

Attach top layer to the housing.

Use adhesive or potting material if needed to fill volume.

ACF attach connection to flex if not connected previously.

The manufacturing process is configurable to simplify the button manufacturing process using advanced manufacturing techniques while optimizing image capture through the molding compounds and/or layers.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A biometric sensor comprising:
a plurality of a first type of signal traces formed on a first surface of a first layer of a multi-layer laminate package;
at least one signal trace of a second type formed on a first surface of a second layer of the multi-layer laminate package;
connection vias in at least the first layer electrically connecting the signal traces of the first type or the signal traces of the second type to respective circuitry of a respective first or second type contained in an integrated circuit physically and electrically connected to one of the first layer, the second layer or a third layer of the multi-layer laminate package,
wherein the first layer comprises a circuit board layer and the second layer comprises a core layer attached to one side of the circuit board layer.

2. The biometric sensor of claim 1 further comprising:
the first type of signal trace comprising drive signal traces and the second type of traces comprising at least one receive signal trace or the first type of traces comprising receive signal traces and the second type of traces comprising at least one drive signal trace.

3. The biometric sensor of claim 1 further comprising:
the at least one trace of the second type comprising one trace of the second type and the sensor comprising a one dimensional linear array capacitive gap biometric sensor.

4. The biometric sensor of claim 1 further comprising:
the at least one trace of the second type comprising a plurality of traces of the second type and the sensor comprising a two dimensional array capacitive biometric sensor.

5. The biometric sensor of claim 1 further comprising:
a third layer comprising a circuit board layer attached to another side of the core layer.

6. The biometric sensor of claim 1 further comprising:
the biometric sensor encapsulated on all sides except for a top finger sensing side and attached to a substrate.

7. The biometric sensor of claim 1 further comprising:
the biometric sensor encapsulated on all sides.

8. The biometric sensor of claim 6 further comprising:
the biometric sensor is encapsulated by moldable plastic material formed around the package by a molding process.

9. The biometric sensor of claim 8 further comprising:
the molding process forming an encapsulation molded with rounded edges and corners.

10. The biometric sensor of claim 1 further comprising:
the biometric sensor comprising a biometric sensor mounted on a portable electronic device.

11. The biometric sensor of claim 10 further comprising:
the biometric sensor cooperating mechanically with elements of a switch within the portable computing device to operate the switch.

12. A method of operating a biometric sensor comprising:
providing a plurality of a first type of signal traces formed on a first surface of a first layer of a multi-layer laminate package;
providing at least one signal trace of a second type formed on a first surface of a second layer of the multi-layer laminate package;
providing connection vias in at least the first layer electrically connecting the signal traces of the first type or the signal traces of the second type to respective circuitry of a respective first or second type contained in an integrated circuit physically and electrically connected to one of the first layer, the second layer or a third layer of the multi-layer laminate package,
wherein the first layer comprises a circuit board layer and the second layer comprises a core layer attached to one side of the circuit board layer.

13. The method of claim 12 further comprising:
the first type of signal trace comprising drive signal traces and the second type of traces comprising at least one receive signal trace or the first type of traces comprising receive signal traces and the second type of traces comprising at least one drive signal trace.

14. The method of claim 12 further comprising:
the at least one trace of the second type comprising a plurality of traces of the second type and the sensor comprising a two dimensional array capacitive biometric sensor.

15. The method of claim 12 further comprising:
a third layer comprising a circuit board layer attached to another side of the core layer.

16. The method of claim 12 further comprising:
the biometric sensor encapsulated on all sides except for a top finger sensing side and attached to a substrate.

17. The method of claim 16 further comprising:
the biometric sensor encapsulated on all sides.

18. The method of claim 16 further comprising:
the biometric sensor is encapsulated by moldable plastic material formed around the package by a molding process.

19. The method of claim 12 further comprising:
the at least one trace of the second type comprising one trace of the second type and the sensor comprising a one dimensional linear array capacitive gap biometric sensor.

\* \* \* \* \*